Figure 1:
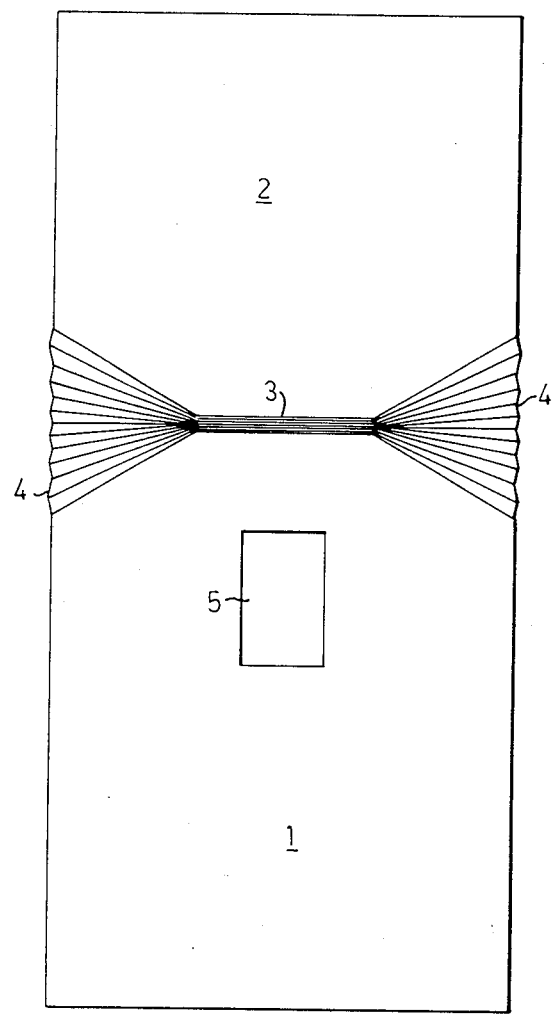

United States Patent [19]
Lundström et al.

[11] Patent Number: 4,574,796
[45] Date of Patent: Mar. 11, 1986

[54] SURGICAL SHEET

[75] Inventors: Thomas Lundström, Göteborg; Carl-Otto Hanssen, Kullavik, both of Sweden

[73] Assignee: Molnlycke AB, Göteborg, Sweden

[21] Appl. No.: 663,042

[22] Filed: Oct. 16, 1984

[30] Foreign Application Priority Data

Oct. 28, 1983 [SE] Sweden .............................. 8305946

[51] Int. Cl.⁴ ............................................. A61F 13/00
[52] U.S. Cl. .................................... 128/132 D; 5/482
[58] Field of Search ................... 128/132 D, 132 R; 5/482, 487, 495, 497, 499; D6/596, 603, 602; 297/225, 219

[56] References Cited

U.S. PATENT DOCUMENTS

| | | | |
|---|---|---|---|
| 768,119 | 8/1904 | Fine | 5/482 |
| 1,701,058 | 2/1929 | Andrade, Jr. | 5/482 |
| 4,308,626 | 1/1982 | Weiss | 5/497 X |

Primary Examiner—Mickey Yu
Attorney, Agent, or Firm—Young & Thompson

[57] ABSTRACT

The present invention relates to a surgical sheet.

A surgical sheet designed in accordance with the invention is formed in a single piece and has a plurality of folds extending across the sheet, substantially in the center thereof. These transverse folds are gathered and joined together at a central region thereof and are intended to be placed adjacent an anesthesis arch. The folds outside the central region are designed to fall in a fan-like fashion on both sides of an operating table, to form vertical screening walls.

1 Claim, 2 Drawing Figures

SURGICAL SHEET

The present invention relates to a surgical sheet comprising a first part with which a patient is covered and a second part which is intended to be draped over an anesthesis arch.

In operating theatres it has hitherto been found problematic to screen, in a simple and satisfactory manner, the anesthestist and associated personnel from the region in which the actual operation is being performed. As a means to this end there is used a so-called anesthesis frame-structure or arch, which is much higher than the operating table and which is intended to support a part of the surgical sheet in a manner to form a vertical screening wall. This wall-forming sheet part is joined with the remainder of the sheet, which is meant to cover the operating table and the patient lying thereon, and to hang down from the sides of the table.

Hitherto it has not been suitable to produce the surgical sheet in one single, continuous length, because of the problems created by such a sheet in the transition region between that part of the sheet which is meant to cover the operation table and that part which is meant to be placed over the anesthesis arch. This arch namely extends laterally beyond the lateral confines of the table, so that those parts of the sheet which, in the vicinity of the arch, hang outside the side edges of the operating table do not fall vertically, but project laterally outwards from these side edges, due to the fact that the sheet continues from the table, up over the screen-forming arch structure. The laterally projecting sheet parts present a troublesome obstacle when operating in the close proximity of the arch; the problems created hereby are particularly acute when performing breast operations.

This problem can be overcome by using a surgical sheet which instead comprises two individual parts, i.e. a first elongated part which is meant to cover the operating table, and a second elongated part which is meant to form a screening partition wall in co-operation with the aforementioned anesthesis arch and which extends transversally to the first sheet part and is joined thereto solely at the region which extends across the width of the operating table, wherewith the overhanging portions of the first sheet will fall vertically, even closely adjacent the screen-forming arch structure. Although such a sheet arrangement solves the problem aforementioned, it has serious inherent disadvantages, since there is not obtained therewith externally of the operating table a vertical screen which extends downwardly from the level of the upper surface of the table.

Surgical sheets are available which have additional sheet-sections for forming a vertical screen on the sides of the operating table, up to the surface level thereof, these sheet parts being joined to the transverse anesthesis sheet-part. These additional sheet-sections are also joined with the side pieces which hang down from the operating table when the sheet is in use, thereby to provide a fully screening vertical partition wall. Although such sheets provide a good screen adjacent the operating table the manufacture of such sheets is particularly complicated, and is probably destined to be done by hand.

The present invention, on the other hand, provides a surgical sheet which can be readily manufactured by machine in one single piece and which is not encumbered with disadvantages inherent in the aforementioned known surgical sheets.

A surgical sheet designed in accordance with the invention is primarily characterized in that the two sheet-parts thereof are substantially of rectangular configuration and preferable of mutually the same width and are together formed in one signle piece with a transition region therebetween, this transition region being provided with a plurality of mutually parallel transverse folds which are joined together in a centre portion of said transition region, whereby parts of the sheet located within the transition region, on both sides of the centre portion, can be swung out in the fashion of a fan, so as to form, when the sheet is in use, substantially vertical screening partitions on both sides of the operating table, these partitions extending from the edge portions of the first sheet-part hanging on both sides of the table to the second sheet-part extending vertically upwards over the anesthesis arch.

Figure 2:
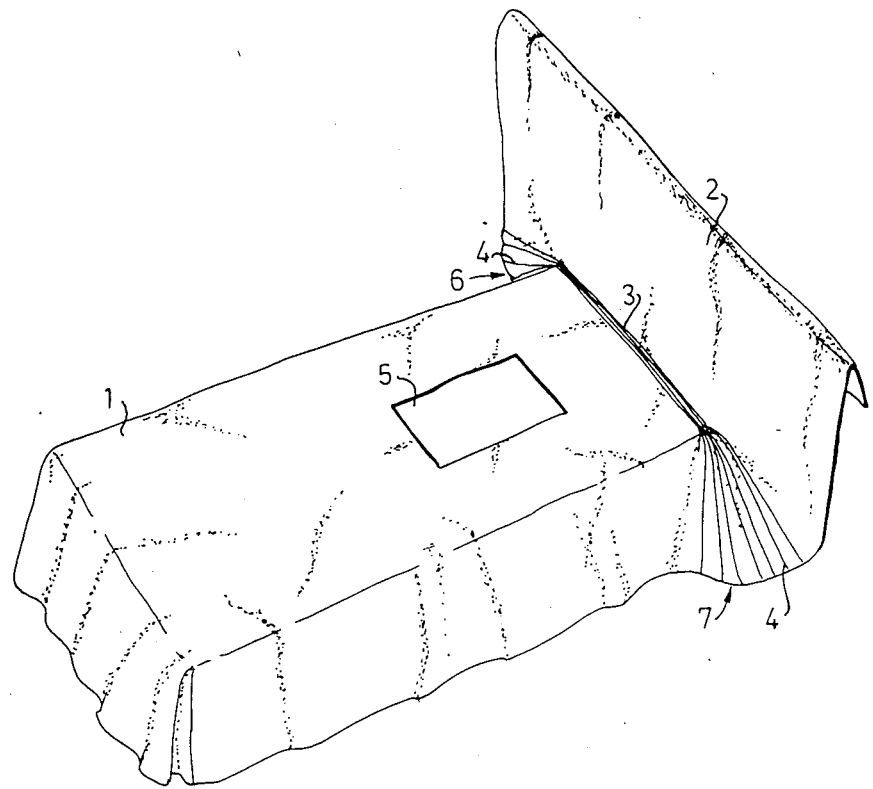

The invention will now be described in more detail with reference to an embodiment thereof illustrated in the accompanying drawing, in which FIG. 1 illustrates a surgical sheet in accordance with the invention, with the sheet shown in a substantially flat state, and FIG. 2 illustrates the sheet in its in-use position, extnding over an operating table with associated anesthesis arch.

The surgical sheet illustrated in the drawings is formed in one single piece from an elongated rectangular blank comprising, for example, a sheet of plastic film to which there has been bonded a layer of non-woven material. The surgical sheet comprises a first part 1, which is intended to be placed over the operating table, and a second part 2, which is intended to be placed over an anesthesis arch. The sheet is provided in a transition region 3 between the first and the second sheet parts with a plurality of transverse, mutually parallel folds 4. The folds 4 are gathered and joined together with the aid of an adhesive or by heat welding, along a central region whose extension substantially corresponds to the width of an operating table. As illustrated in the drawings, the folds on both sides of this central gathered region can be opened out in a fan-like fashion. The sheet-part 1 has provided therein a conventional opening 5, which is intended to be positioned over that part of the patient where an operation is to be performed.

As illustrated in FIG. 2, when the surgical sheet is in use, the first sheet-part 1 is placed over the operating table and the patient lying thereon. The second sheet-part 2 is placed over the anesthesis arch with the folds 4 located substantially opposite the arch. The folds 4 fall in fan-like fashion on both sides of the operating table and form vertical screening walls or partitions 6,7 beneath those parts of the second sheet-part 2, which hangs vertically over the anesthesis arch, located laterally of the operating table on respective sides thereof.

The invention is not restricted to the described embodiment, and various modifications can be made within the scope of the claim.

For example the second sheet-part 2 can be wider than the first sheet-part 1, and the sheet can comprise other materials than those mentioned.

We claim:

1. A surgical sheet having a patient-covering first sheet-part and a second sheet-part which is joined with the fist sheet-part and which is intended to be placed over an anesthesis arch, characterized in that the two sheet-parts are substantially of rectangular shape and preferably of mutually the same width, and are both formed in one and the same sheet length with a portion of said sheet as a transition region located therebetween; in that the transition region is provided with mutually parallel folds of said sheet which are gathered and joined together at a central part of said transition region, whereby parts of the sheet located within said transition region and on both sides of the central part can swing out in a fan-like fashion in a manner to form substantially vertical screening partition walls on both sides of an operating table when the sheet is in use, these walls extending from edge regions of the first sheet-part hanging down on both sides of said table to the second sheet-part extending vertically upwards over the anesthesia arch.

* * * * *